(12) United States Patent
Parker

(10) Patent No.: US 6,749,063 B2
(45) Date of Patent: Jun. 15, 2004

(54) ENDOSCOPE TRANSPORTATION DEVICE

(75) Inventor: George Christopher Parker, Westcliffe-on-Sea (GB)

(73) Assignee: Medicart International Limited (GB)

( * ) Notice: Subject to any disclaimer, the term of this patent is extended or adjusted under 35 U.S.C. 154(b) by 0 days.

(21) Appl. No.: 10/146,222

(22) Filed: May 14, 2002

(65) Prior Publication Data
US 2003/0078472 A1 Apr. 24, 2003

(30) Foreign Application Priority Data
Oct. 24, 2001 (GB) .............................................. 0125478

(51) Int. Cl.⁷ .............................................. B65D 83/10
(52) U.S. Cl. ................... 206/363; 206/564; 220/495.06
(58) Field of Search ................. 206/363, 364, 206/365, 366, 370, 564, 438; 220/495.01–495.03, 495.06, 495.08, 495.11

(56) References Cited

U.S. PATENT DOCUMENTS

| | | | | |
|---|---|---|---|---|
| 1,592,726 A | * | 7/1926 | Dunbar | 220/592.2 |
| 4,574,978 A | * | 3/1986 | Hodges | 220/403 |
| 4,948,266 A | * | 8/1990 | Bencic | 383/34 |
| 5,108,195 A | * | 4/1992 | Perron | 383/10 |
| 5,295,606 A | * | 3/1994 | Karwoski | 220/403 |
| 6,029,844 A | * | 2/2000 | Brady | 220/495.08 |
| 6,139,185 A | * | 10/2000 | Hamilton et al. | 383/11 |
| 6,151,910 A | * | 11/2000 | Hazen | 220/592.2 |
| 6,305,567 B1 | * | 10/2001 | Sulpizio | 220/495.11 |
| 6,378,721 B1 | * | 4/2002 | Williams | 220/495.08 |

* cited by examiner

*Primary Examiner*—Shian Luong
(74) *Attorney, Agent, or Firm*—Renner, Kenner, Greive, Bobak, Taylor & Weber

(57) ABSTRACT

A device for in-hospital transportation of flexible medical endoscopes comprises: a re-usable tray having an inner compartment defined by a generally planar base, surrounding walls upstanding therefrom, and peripheral lip-portion(s) provided at least partially around said surrounding walls and extending outwardly therefrom; a single-use, disposable tray-liner having margins to embrace and to detachably-engage at least a major part of said peripheral lip-portion(s) thereof; an open-faced pouch provided centrally of said margins, such that in use said pouch is able to conform itself substantially to the inner compartment of the re-usable tray; and a pouch-closing protective cover which in use is capable of being extended from one edge across an open-face of the pouch supported in the inner compartment and detachably secured so as safely to enclose an endoscope when it is within the pouch within the inner compartment.

24 Claims, 3 Drawing Sheets

ENDOSCOPE TRANSPORTATION DEVICE

BACKGROUND TO THE INVENTION (a) Field of the Invention

This invention relates to a device for the in-hospital transportation of medical equipment, particularly flexible medical endoscopes, both before and after use.

Flexible medical endoscopes are used for the internal examination of various parts of the human or animal body. They are produced in diameters ranging from 0.02 to 0.6 in (0.5 to 15 mm) and with lengths of 12 to 120 in (300 to 3000 mm). The majority have internal channels, down which air, water or accessories may be directed so as to facilitate examinations, or to carry out surgical procedures. A modern electronic or video endoscope is a relatively expensive piece of equipment, typically costing in the region of US$30,000 (GB£20,000).

Due to the invasive nature of many of the procedures for which flexible medical endoscopes are used, it is necessary that they be thoroughly cleaned and disinfected prior to and after each use.

(b) Description of Prior Art

Ideally, the room in which the cleaning and disinfection are carried out should be in fairly close proximity to the operating theatre or procedure room. However, this ideal is seldom achieved, and this results in endoscopes being carried over fairly long distances both prior to, and after, being used on a patient.

The present invention has been developed, following experience in hospital departments carrying out flexible endoscopy over many years and in many countries, including the United States, Germany, France, Japan and the United Kingdom. The methods of carrying endoscopes between the procedure room and the cleaning room vary little between one country and another, or with the elapse of time, and would generally be considered unsatisfactory, based on such criteria as:

protection of the endoscope both before and after use, against accidental damage or contamination;

protection of the staff, patients, and workplace against contamination, and possible infection, deriving from a used and uncleaned endoscope; and protection of unused endoscopes against the potential for cross-contamination from contact with used endoscopes carrying infectious matter or with any surface that has previously been in contact with a contaminated endoscope.

Furthermore, at least in the United Kingdom and France, the recent BSE (Bovine Spongiform Encephalopathy) crisis has led to heightened concerns that the human form, Creutzfeldt-Jakob Disease (CJD), may be transmitted by contaminated endoscopes. Moreover, the recent re-emergence of tuberculosis also presents a threat of air-borne contamination, in areas where endoscopes are being used and transported.

SUMMARY OF THE INVENTION

The present invention seeks to address all the above problems of moving flexible endoscopes from one area to another in a safe and hygienic way, thus without exposing anyone or anything to contamination. The present invention has been developed particularly for use in transporting flexible medical endoscopes, and hence is described herein with particular reference to that use. Nevertheless, it will be appreciated that the present invention may also find use in the transportation of other medical equipment and/or any other situation where it is important that cleanliness be maintained or contamination be contained.

According to the present invention, there is provided a device for in-hospital transportation of flexible medical endoscopes, both before and after use, which device comprises:

a re-usable tray having a downwardly-dished, inner compartment defined by a generally planar base, surrounding walls upstanding therefrom, and peripheral lip-portion(s) provided at least partially around said surrounding walls and extending outwardly therefrom, said tray being formed of a semi-rigid material which is capable of withstanding repeated disinfection, and being so constructed and dimensioned as when in use to provide support for an endoscope coiled in a stress-free state therewithin; and a single-use, disposable tray-liner having margins extensive enough to be able when assembled with the underlying tray to embrace and to detachably-engage at least a major part of the lip-portion(s) thereof and be thereby removably retained thereon, and an open-faced pouch provided centrally of said margins, and being so constructed and dimensioned that in use said pouch is able to conform itself to the contours of the dished endoscope compartment of the underlying tray, said tray-liner being formed of a flexibly deformable, sheet material impermeable to bodily fluids; and a pouch-closing protective cover which in use can be extended from one edge across the open-face of the liner pouch supported in the inner compartment and suitably but detachably secured to the other edge thereof so as safely to enclose and protect the endoscope when it is within the liner-pouch within the inner compartment, said cover being formed of a material similar to that of the tray-liner.

It is envisaged that the pouch-closing protective cover may be supplied either integrally with or affixed to the tray liner, or even as a separate component.

The term "margins" as used herein refers to those portions of the liner which, when assembled with the underlying tray, are folded over the apex of the tray walls to engage with the peripheral lip-portions extending externally around the tray. The margins may conveniently be no more than upper portions of walls defining the liner pouch, or may alternatively be formed as a distinct, though still integral, component of the liner.

BRIEF DESCRIPTION OF THE DRAWINGS

Preferred embodiments of the present invention will now be described, by way of example only, with reference to the accompanying drawings, in which.

DESCRIPTION OF PREFERRED EMBODIMENTS

Figure 1:
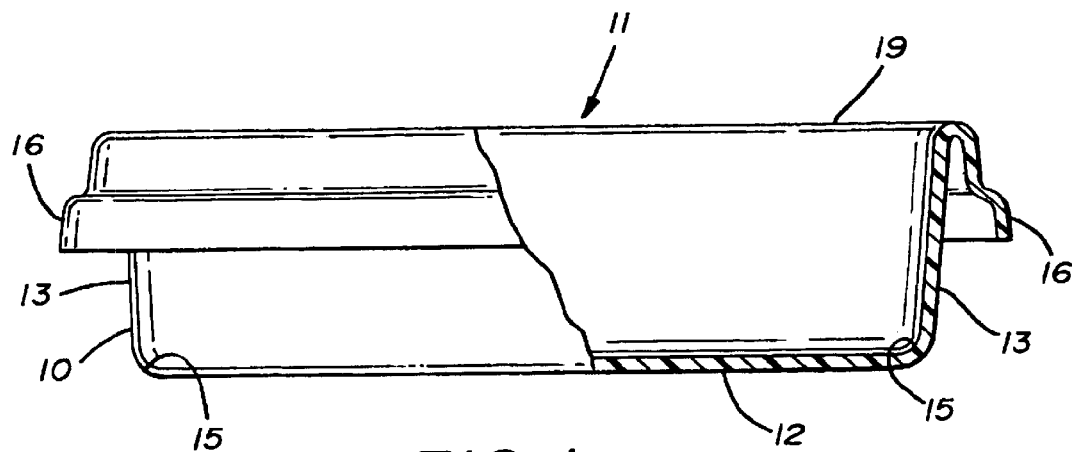
FIG. 1 is a partly cut-away side-view of a tray having an endoscope compartment therewithin, for use in the endoscope transportation device of the present invention.

In preferred embodiments of the present invention, the dished endoscope compartment within the reusable tray may be of other regular or even irregular outline in plan view, but it is most conveniently of generally-rectangular outline.

The dimensions of the tray must be sufficient to accommodate therein substantially all sizes of flexible medical endoscope in a coiled state without undue stress being applied to the flexible portions thereof. However, the tray must also be sufficiently small to permit it to be easily carried by a person.

Therefore, it is preferred that the external dimensions of the tray are: a length of about 21 in (525 mm), a width of about 17 in (425 mm), and a depth of about 4.2 in (105 mm).

The corresponding internal dimensions of the endoscope compartment within the tray are preferably: a length of about 18.8 in (470 mm), and a width of about 14.8 in (370 mm).

So that the endoscope may be safely coiled within the endoscope compartment without any undue danger of resultant damage to its flexible parts, it is highly desirable that all the corners and intersections between the walls of the endoscope compartment and with its base shall be smoothly curved rather than sharply angular, so that they merge imperceptibly with one another and with the base of the endoscope compartment. This provides the endoscope compartment with smooth internal surfaces wherein the junctions between each wall and its next adjacent walls and also the junctions between each wall and the base are all in the form of rounded corners having a large radius of curvature.

This moreover has a further important advantage, because the fact that the junctions between the walls and with the base are all smoothly rounded eliminates any sharply angular nooks or crannies which otherwise might harbour dirt and bacteria. The cleaning and disinfection of the reusable tray are therefore greatly facilitated by thus providing it with smooth internal surfaces.

The tray is preferably formed from moulded plastics material, most preferably A.B.S. Preferably the tray is formed so as to have a sheet thickness of about 0.16 in (4 mm).

The open-faced pouch of the liner needs to be such as will loosely adapt itself to the contours of the endoscope compartment in the underlying tray. The pouch itself therefore will in a sense be defined by opposed generally-vertical walls surrounding a generally-horizontal basal area roughly coextensive with the planar base of the tray. The upper ends of the walls define the open face of the pouch, where they meet with or form the margins of the tray-liner at the level of the rim of the underlying tray.

The lower ends of the side walls then come together to define the closed bottom of the pouch. It would perhaps be ideal (at least from the viewpoint of appearance) if the lower ends of the vertical side walls were to be interconnected by a horizontal flat sheet of material more or less coextensive with the planar base of the underlying tray, so that the liner fits snugly within the tray compartment.

However it must be remembered that the tray-liner is a single-use, disposable thing, with little need for an aesthetic appearance. Any form of pouch that will serve its intended purpose can therefore be adopted, irrespective of aesthetics.

Bearing that in mind, it may be most appropriate to adopt a more ill-fitting construction of pouch which however is simpler and therefore more economic to manufacture. In one embodiment of liner for use in the present invention, the lower ends of the side walls proper are further extended and gathered together, with suitable folding and pleating, to meet more or less centrally of the bottom of the pouch and are there integrated with one another at a junction point or more usually a junction seam.

This kind of less aesthetic but more economic construction of pouch is indeed illustrated in the accompanying drawings in relation to an endoscope compartment in the tray and correspondingly a pouch in the liner both of generally rectangular outline, and as there appears the side and end walls proper are notionally further extended downwards but in fact are folded and pleated together, to meet at a seam more or less centrally of the pouch bottom. When thus constructed and in free-hanging posture (rather than supported within the endoscope compartment of the underlying tray) of course the pouch bottom will tend to sag down, and the side and end walls will appear to taper inwards until they are gathered and integrated together into a relatively deep and rather baggy pouch.

In an alternative, and currently preferred, embodiment of the present invention, the tray-liner is made by a so-called "thermo-forming" process, from a single piece of flexibly deformable sheet material, and thus has no apparent seams. Preferably, the sheet material is a plastics material, and most preferably is high density polythene (HDP).

For ease of handling, the protective cover may be pre-attached on or around the margins of the liner so as thereby to form a flap of the liner, either attached to or integral with the liner along a side of the margins corresponding to one of the walls of the pouch therein.

In this embodiment of the present invention, the pouch-closing cover of the liner may be provided with fixing means along a free side thereof, preferably the free side remote from the line of attachment/integration between liner and cover. In use, this enables said free side of the cover to be detachably secured to another side of the pouch when supported in the endoscope compartment. It is in fact greatly preferred that the cover should be provided with fixing means along at least two or even all the free sides thereof.

The fixing means may be any of any suitable kind, for instance a Zip®-fastener, a Velcro®-fastener or a press-stud closure, but these are relatively expensive for a single-use, disposable item, and so with economy in mind the fixing means is preferably an adhesive strip.

However, for reasons of economy of manufacture, amongst other things, it is generally preferred that the protective cover be provided as a separate component, to be temporarily secured at or around the margins of the liner when in use.

Where the protective cover is a separate component of the kit of parts, it should be so shaped and dimensioned as in use to embrace, and thereby be detachably secured to, the top of the endoscope compartment in a snug-fitting arrangement. This may be achieved by the provision of an elasticated skirt around the perimeter of the cover.

In a further preferred embodiment of the present invention, the protective cover is reversible and carries an indication on either side thereof of the status of the endoscope contained within the tray. In practice, this may be no more than the printing of the words "clean" and "contaminated" (or similar) on either side of the reversible cover. The reversible cover must of course by capable of being temporarily secured to an upper portion of the walls of the endoscope compartment in both its normal and reversed positions. The cover, when provided as a separate component is preferably formed of a plastics material, most preferably low density polythene (LDP).

In a still further embodiment of the present invention, there is provided a rigid lid adapted to fit snugly over the top of the protective cover when fitted on the tray, so as to provide protection against accidental piercing of the flexible cover.

Alternatively, the cover, or indeed the entire liner, may advantageously be formed from a self-sealing plastics material, such as a suitable grade of so-called "cling film", thus eliminating the need for the separate provision of fixing means.

The liner should be capable of co-operating with the tray in such a way that the margins thereof may be folded over externally of the endoscope compartment to engage with the peripheral lip-portion(s).

When using a generally-rectangular tray of the preferred dimensions, it is as regards the liner preferred that it should have an overall length of about 20.8 in (520 mm), a width of about 15.2 in (380 mm), and a depth of about 14.4 in (360 mm). The liner cover then preferably has a width of about 20.4 in (510 mm) so as to extend across the endoscope compartment.

In a particularly preferred embodiment of the present invention, the material(s) from which the tray, the liner and/or the protective cover is/are formed will preferably be impregnated with an anti-bacterial or other biocidal or biostatic agent.

The peripheral lip-portions around the walls of the tray are intended not only for anchoring the tray liner therein but also to serve as a kind of handle for carrying the tray manually.

In a further preferred embodiment of the present invention, there is further provided a trolley having support points adapted to receive and support the peripheral lip-portion(s) of one or more trays.

A particular embodiment of endoscope transportation device according to the present invention will now be described with reference to the accompanying FIGS. 1 to 6.

Figure 2:
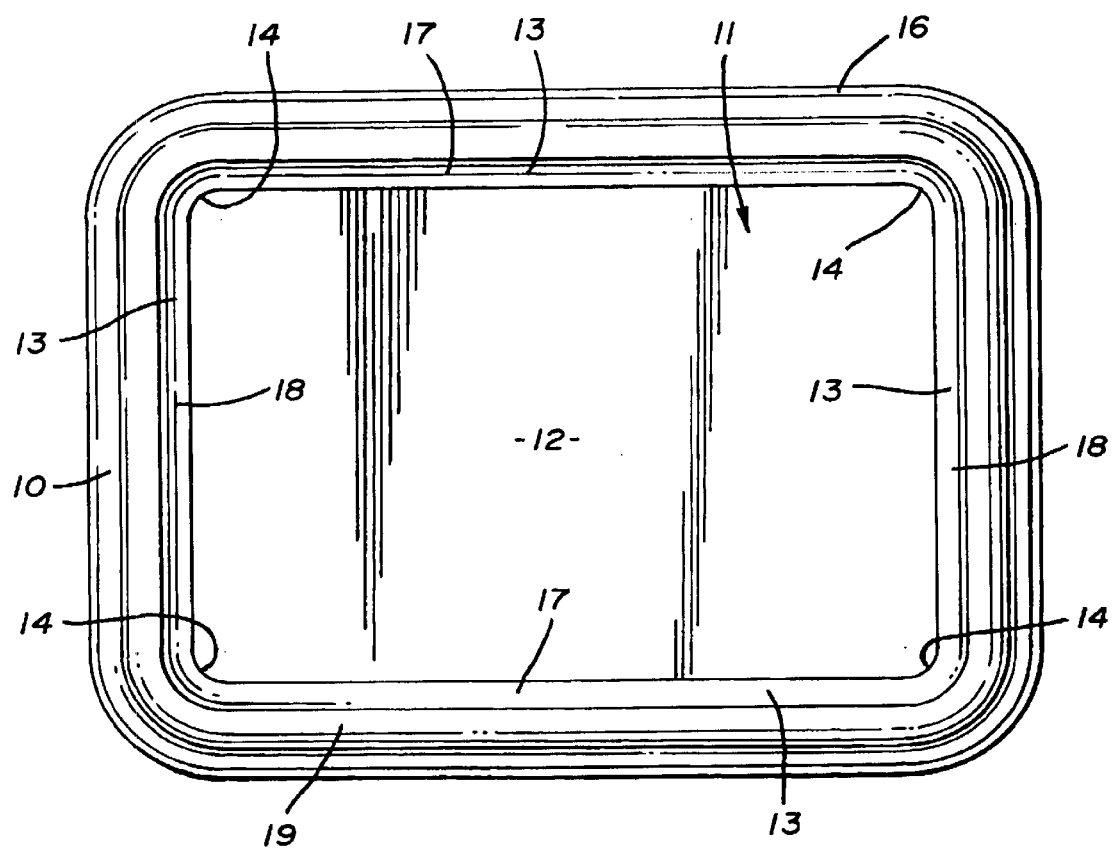
FIG. 2 is a plan view from above of the tray of FIG. 1.

Referring first to FIGS. 1 and 2, there is shown a tray 10, having a downwardly-dished inner endoscope compartment, generally indicated 11 therewithin. The endoscope compartment is defined by a generally rectangular base 12 with surrounding walls 13 upstanding therefrom.

Each wall 13 is curved at each end and at the bottom thereof, such that each wall 13 merges imperceptibly with each next adjacent wall 13, and with the base 12. Thus, the junctions 14 between adjacent walls 13, and the junctions 15 between each wall and the base 12, take the form of rounded corners having a large radius. The upper edges of the end walls 13 are curled over to form a peripheral lip portion 16 externally around the walls 13. A brim 19 around the tray 10 is defined at the uppermost point of the walls 13.

As is best shown in FIG. 2, the walls 13 which define the endoscope compartment 11, comprise a pair of opposed side walls 17, and a pair of opposed end walls 18. The endoscope compartment 11 is required to be large enough to accommodate substantially all sizes of flexible medical endoscope therewithin without undue stress being applied to the flexible portions thereof, yet must at the same time be small enough to permit the tray 10 to be easily carried by a person. In order to achieve this result, the side walls 17 have a length of about 21 in (525 mm), whilst the end walls have a length of about 17 in (425 mm). The depth of the endoscope compartment 11, (that is to say the height of the walls 13) is about 4.2 in (105 mm).

Figure 3:
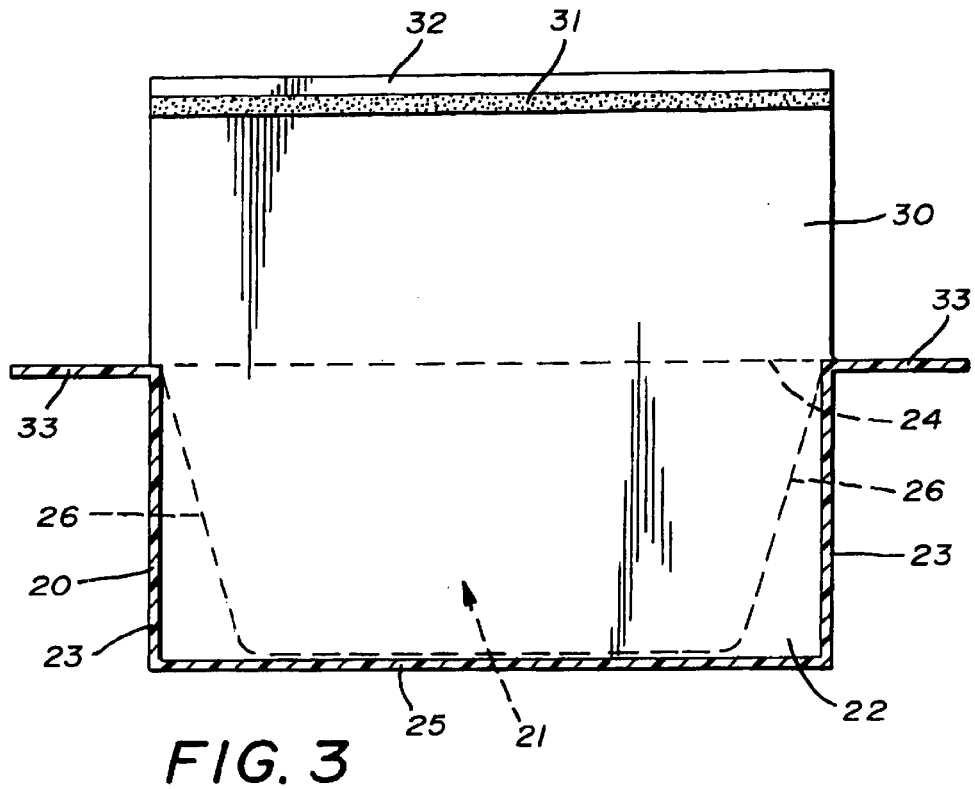
FIG. 3 is a diagrammatic side-view of a disposable liner for use in conjunction with the tray of FIGS. 1 and 2 in the endoscope transportation device of the present invention.

Referring now to FIG. 3, there is shown a disposable liner 20 for use in conjunction with the tray 10 to form the endoscope transportation device of the present invention. The liner 20 has a pouch, generally indicated 21, defined by a pair of opposed side walls 22 and a pair of opposed end walls 23. The upper edges of the opposed side walls 22 and the opposed end walls 23 form a rim 24 defining the open end of the pouch 21, whilst the lower edges of the opposed side walls 22 in this embodiment meet at a seam 25 which defines the closed end of the pouch 21. The opposed end walls 23 are provided with fold lines 26, and taper inwards to meet the seam 25. However, as noted above, it is currently preferred that the liner 20 be formed so as to have no apparent seams.

The liner 20 has margins 33 adjacent the open end of the pouch 21, which although shown in FIG. 3 as distinct, though still integral, components of the liner 21, may conveniently be no more than the upper portions of the walls 22, 23 defining the pouch 21.

A cover 30 is provided along a side of the rim 24 corresponding to one of the opposed side walls 22. The cover 30 is provided with an adhesive strip 31 adjacent its free end 32. While the cover 30 as shown in FIG. 3 is integral with the liner 20, it may preferably be provided as a separate component of the present invention, as will be described subsequently with reference to FIG. 6.

Figure 4:
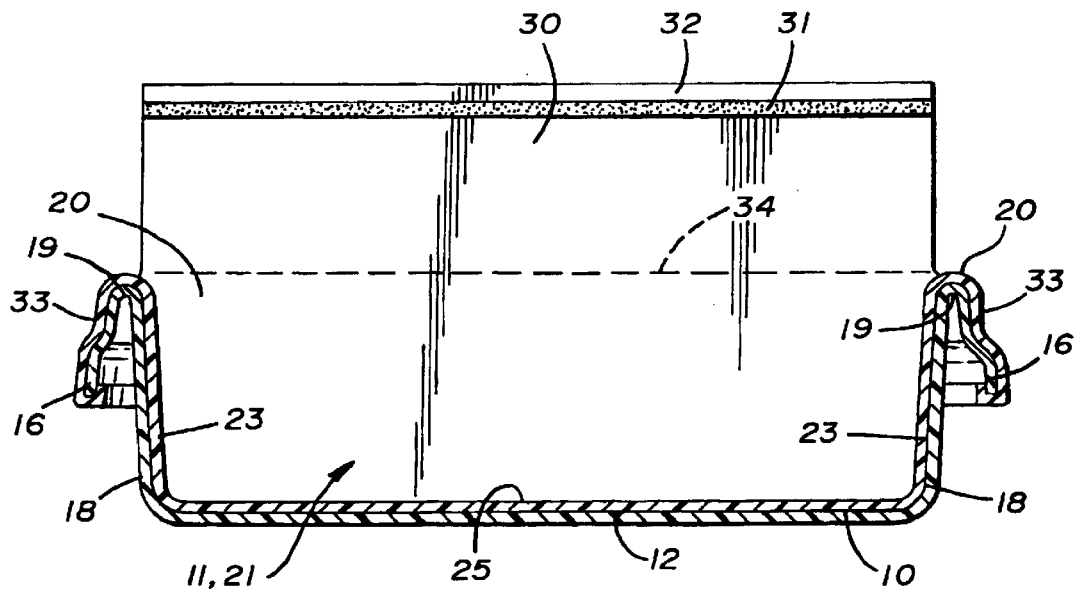
FIG. 4 is a cross-sectional view showing the tray of FIGS. 1 and 2 in combination with the line of FIG. 3 to from the endoscope transportation device of the present invention.

As is best shown in FIG. 4, in use the liner 20 is placed into the tray 10. The margins 33 of the liner 20 are folded over the brim 19 of the tray 10, to engage with the peripheral lip 16 around the tray 10.

The liner 20 is formed of a flexibly deformable sheet material such as high density polythene, so that it may be conformed to the contours of the underlying tray 10. Thus, the pouch 21 takes on the general shape of the endoscope compartment 11, with the side walls 22 of the liner 20 corresponding to the side walls 17 of the tray 10, and the end walls 23 of the liner 20 corresponding to the end walls 18 of the tray 10. The seam 25 defining the closed end of the pouch 21 is located against the base 12 of the tray 20.

The length of the liner 20 (i.e.: the length of the side walls 22) should be substantially equal to the corresponding length of the tray 10, whilst the width of the liner (i.e.: the length of the end walls 23) should be somewhat shorter than the corresponding width of the tray 10. This enables the liner 20 to be gently stretched across the width of the tray 10, thus holding the liner 20 in a state of tension. Therefore, in the preferred embodiment, the length of the side walls 22 of the liner is about 20.8 in (520 mm), whilst the length of the end walls 23 is about 15.2 in (380 mm). The preferred depth of the liner 20 is about 14.4 in (360 mm).

The margins 33 of the liner 20, when engaged with the lip 16 of the tray 10, are located some way below the brim 19 of the tray. It is therefore necessary that the length of the cover 30 be substantially greater than the width of the tray 10. This enables the cover 30 to be folded along a fold line 34 co-incident with the brim 19 of the tray, and to extend across the width of the tray 10 to be secured on the opposed side wall 17/22 thereof, by means of the adhesive strip 31.

In use, a clean liner 20 is engaged with the tray 10 as described above. A cleaned and disinfected endoscope (not shown) may then be placed in the lined endoscope compartment 11/21. The cover 30 is then folded across the top of the lined tray 10/20 and secured at the opposite side 17/22 by means of the adhesive strip 31, so as to isolate the endoscope from any potential airborne contamination. The lined tray 10/20 with the endoscope enclosed therein may then be transported to the procedure room, either by being manually carried, using the lip 16 as a handle, or using a trolley (not shown) having connection points adapted to receive the lip 16 of one or more trays.

When the endoscope is to be used, the cover 30 is detached from its fixing point, and the endoscope may then be removed from the lined endoscope compartment 11/21. Once the endoscopy procedure is complete, the endoscope may be placed back into the lined endoscope compartment 11/21, and the cover 30 is re-sealed by means of the adhesive strip 31. The lined tray 10/20 is then transported back to the cleaning room, where the cover 30 is again detached from its fixing point, and the endoscope removed for cleaning and disinfecting. The used liner 20 is then removed from the tray 10, disposed of as contaminated waste, and replaced with a clean liner 20.

Figure 5:
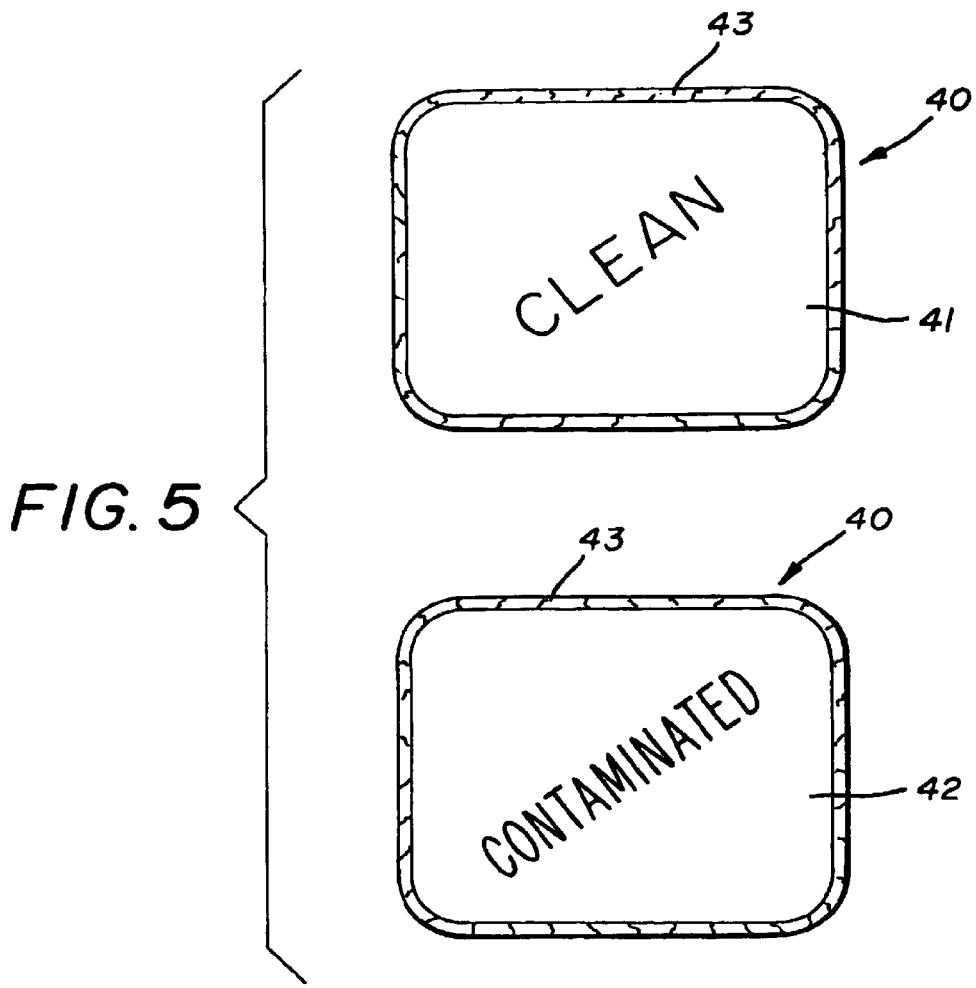
FIG. 5 is a plan view of a reversible protective cover for use in conjunction with the tray of FIGS. 1 and 2 in the endoscope transportation device of the present invention.

Referring now to FIG. 5, there is shown an alternative construction of protective cover, generally indicated as 40, for use in conjunction with the tray 10 and liner 20 to form the endoscope transportation device of the present invention.

The cover 40 is reversible, and has printed on a first side 41 thereof, the word "CLEAN", and on its second side 42 thereof, the word "CONTAMINATED". The cover 40 is provided with an elasticated skirt 43, by means of which the cover 40 may be attached to an upper portion of the walls 13 of the endoscope compartment 11, with either its first 41 or second 42 sides uppermost. The status of an endoscope within the endoscope compartment 11 can thus be indicated.

Figure 6:
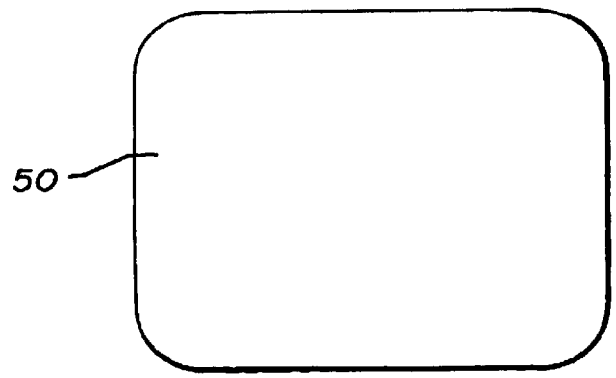
FIG. 6 is a plan view of a rigid lid, for use in the endoscope transportation device of the present invention.

As shown in FIG. 6, a rigid lid 50 may be provided to fit snugly over the protective cover 40 to protect it from accidental piercing.

What is claimed is:

1. A device for in-hospital transportation of flexible medical endoscopes, both before and after use, which device comprises:

a re-usable tray having a downwardly-dished, inner compartment defined by a generally planar base, surrounding walls upstanding therefrom, and peripheral lip-portions provided at least partially around said surrounding walls and extending outwardly therefrom, said re-usable tray being formed of a semi-rigid material which is capable of withstanding repeated disinfection, and being so constructed and dimensioned as when in use to provide support for a flexible medical endoscope coiled in a stress-free state therewithin; and a single-use, disposable tray-liner having margins extensive enough to be able when assembled with the re-usable tray to embrace and to detachably-engage at least a major part of said peripheral lip-portions thereof and be thereby removably retained thereon, and an open-faced pouch provided centrally of said margins and being so constructed and dimensioned that in use said pouch is able to conform itself substantially to the downwardly-dished inner compartment of the re-usable tray, said tray-liner being formed of a flexibly deformable, sheet material substantially impermeable to bodily fluids; and a pouch-closing protective cover which in use is capable of being extended from one edge across said open-face of the pouch supported in the inner compartment and suitably but detachably secured to another edge thereof so as safely to enclose and protect an endoscope when it is within the pouch within the inner compartment, said cover being formed of a flexibly deformable sheet material, substantially impermeable to bodily fluids, said protective cover being provided as a separate component, to be temporarily secured on or around said margins of the tray-liner when in use, and so shaped and dimensioned as in use to embrace and thereby be detachably secured to an upper portion of said walls, and being reversible, and capable of being temporarily secured to an upper portion of said walls, in both its normal and reversed positions.

2. A device as claimed in claim 1, wherein said inner compartment within the reusable tray is of generally-rectangular outline.

3. A device as claimed in claim 1, in which all corners and intersections between said walls and with said base of the inner compartment are smoothly curved so that they merge imperceptibly with one another.

4. A device as claimed in claim 1, wherein said tray is formed from moulded plastics material.

5. A device as claimed in claim 1, wherein said reversible cover carries on each side thereof an indication of the status of an endoscope contained within said inner compartment.

6. A device as claimed in claim 1, wherein said cover is formed from a self-sealing plastics material.

7. A device as claimed in claim 1, wherein said protective cover is provided with an elasticated skirt, so as temporarily to secure it to an upper portion of said walls.

8. A device as claimed in claim 1, wherein said cover is shaped so as in use to embrace an upper portion of said walls in a snug-fitting arrangement.

9. A device as claimed in claim 1, wherein said liner is formed from one piece of sheet material.

10. A device as claimed in claim 1, wherein material from which at least one of said tray and said liner is formed, is impregnated with an anti-bacterial agent.

11. A device as claimed in claim 1, wherein said peripheral lip-portions are adapted for use as a handle for carrying the tray manually.

12. A device as claimed in claim 1, further comprising a rigid lid adapted to fit snugly around an upper portion of the walls of said inner compartment above said protective cover.

13. A device for in-hospital transportation of flexible medical endoscopes, both before and after use, which device comprises:

a re-usable tray having a downwardly-dished, inner compartment defined by a generally planar base, surrounding walls upstanding therefrom, and peripheral lip-portions provided at least partially around said surrounding walls and extending outwardly therefrom, said re-usable tray being formed of a semi-rigid material which is capable of withstanding repeated disinfection, and being so constructed and dimensioned as when in use to provide support for a flexible medical endoscope coiled in a stress-free state therewithin; and a single-use, disposable tray-liner having margins extensive enough to be able when assembled with the re-usable tray to embrace and to detachably-engage at least a major part of said peripheral lip-portions thereof and be thereby removably retained thereon, and an open-faced pouch provided centrally of said margins and being so constructed and dimensioned that in use said pouch is able to conform itself substantially to the downwardly-dished inner compartment of the re-usable tray, said tray-liner being formed of a flexibly deformable, sheet material substantially impermeable to bodily fluids; and a pouch-closing protective cover which in use is capable of being extended from one edge across said open-face of the pouch supported in the inner compartment and suitably but detachably secured to another edge thereof so as safely to enclose and protect an endoscope when it is within the pouch within the inner compartment, said cover being formed of a flexibly deformable sheet material substantially impermeable to bodily fluids, said protective cover being pre-attached to the tray-liner at the margins of said liner along a side of the margins corresponding to a wall of said pouch defined therein.

14. A device as claimed in claim 13, wherein said inner compartment within the reusable tray is of generally-rectangular outline.

15. A device as claimed in claim 13, in which all corners and intersections between said walls and with said base of the inner compartment are smoothly curved so that they merge imperceptibly with one another.

16. A device as claimed in claim 13, wherein said tray is formed from moulded plastics material.

17. A device as claimed in claim 13, wherein said cover is provided with fixing means along at least a free side thereof remote from said side along which said cover and said liner are attached.

18. A device as claimed in claim 16, wherein said cover is provided with fixing means along all free sides thereof.

19. A device as claimed in claim 16, wherein the said fixing means is an adhesive strip.

20. A device as claimed in claim 13, wherein said cover is shaped so as in use to embrace an upper portion of said walls in a snug-fitting arrangement.

21. A device as claimed in claim 13, wherein said liner is formed from one piece of sheet material.

22. A device as claimed in claim 13, wherein material from which at least one of said tray and said liner is formed, is impregnated with an anti-bacterial agent.

23. A device as claimed in claim 13, wherein said peripheral lip-portions are adapted for use as a handle for carrying the tray manually.

24. A device as claimed in claim 13, further comprising a rigid lid adapted to fit snugly around an upper portion of the walls of said inner compartment, above said protective cover.

* * * * *